US008268258B2

(12) United States Patent
Niederberger et al.

(10) Patent No.: US 8,268,258 B2
(45) Date of Patent: Sep. 18, 2012

(54) PACKAGE FOR AN OBJECT HAVING A HYDROPHILIC SURFACE COATING

(75) Inventors: Brigitte Niederberger, Thalwil (CH); Irio Giuseppe, Arth (CH); Michael Glauser, Rotkreuz (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 625 days.

(21) Appl. No.: 12/362,703

(22) Filed: Jan. 30, 2009

(65) Prior Publication Data

US 2009/0198119 A1 Aug. 6, 2009

Related U.S. Application Data

(63) Continuation of application No. PCT/EP2007/057939, filed on Aug. 1, 2007.

(30) Foreign Application Priority Data

Aug. 2, 2006 (EP) .................................... 06016067

(51) Int. Cl.
*G01N 33/48* (2006.01)

(52) U.S. Cl. ........ 422/430; 422/502; 422/503; 422/504; 422/507

(58) Field of Classification Search .................. 422/430, 422/502–504, 507
See application file for complete search history.

(56) References Cited

U.S. PATENT DOCUMENTS

| | | | | |
|---|---|---|---|---|
| 3,532,412 | A | 10/1970 | Miller | |
| 5,766,473 | A | 6/1998 | Strobel et al. | |
| 5,934,494 | A | 8/1999 | Takahashi et al. | |
| 6,080,350 | A * | 6/2000 | Hekal | 264/255 |
| 6,871,419 | B1 * | 3/2005 | Becker et al. | 34/416 |
| 7,829,023 | B2 * | 11/2010 | Burke et al. | 422/82.01 |
| 2003/0087292 | A1 | 5/2003 | Chen et al. | |
| 2003/0175155 | A1 * | 9/2003 | Charlton | 422/61 |
| 2004/0028931 | A1 | 2/2004 | Bletsos et al. | |
| 2006/0216570 | A1 * | 9/2006 | Vyas et al. | 429/38 |

FOREIGN PATENT DOCUMENTS

| | | | |
|---|---|---|---|
| EP | 1360935 | A1 | 12/2003 |
| WO | WO 2006/021361 | A2 | 3/2006 |

OTHER PUBLICATIONS

Aizawa et al. "Turning of Contact Angles on Glass Plates Coated with Plasma-Polymerized Styrene, Allylamine and Acrylic Acid". Materials Science and Engineering C 12 (2000), pp. 49-54.*

International Preliminary Report on Patentability for International Application PCT/EP2007/057939.

International Search Report for International Application PCT/EP2007/057939.

* cited by examiner

*Primary Examiner* — In Suk Bullock
*Assistant Examiner* — Paul Hyun
(74) *Attorney, Agent, or Firm* — Faegre Baker Daniels LLP

(57) ABSTRACT

A package for an object having a hydrophilic surface includes at least one of a loose cover for the hydrophilic surface and an adsorbing surface, the affinity of which for apolar gases is equal to or greater than that of the hydrophilic surface.

26 Claims, 2 Drawing Sheets

12
20
22
18
14
12
16
20
10

PACKAGE FOR AN OBJECT HAVING A HYDROPHILIC SURFACE COATING

The present application is a continuation application of and claims priority to PCT Application Serial No. PCT/EP2007/057939, filed on Aug. 1, 2007, which in turn claims priority to EP Application Serial No. EP06016067.8, filed on Aug. 2, 2006. All prior applications are hereby expressly incorporated into the present application by reference.

FIELD OF THE DISCLOSURE

The present disclosure relates to a package for an object having a hydrophilic surface.

BACKGROUND AND SUMMARY OF THE DISCLOSURE

Hydrophilic surfaces and in particular surfaces which have a hydrophilic coating are used especially for microfluidic elements (i.e., microstructures through which a liquid should flow). Such microfluidic elements are used especially in analytical systems for body fluids, for example in blood sugar measuring instruments which enable diabetics to self-monitor their blood sugar level. In this case, the microfluidic test element can comprise a lancing member which is provided with or connected to a microchannel for the capillary transport of the body fluid. Examples of such microneedles or microsamplers are disclosed in WO 2006/021361, and are usually provided as disposable parts.

The microchannel and, where appropriate, the lancing member should be made out of a biocompatible material which can be mechanically stressed and sterilized in a simple manner. Surgical steel is particularly suitable for this, but its hydrophilicity is too low to allow a capillary transport of aqueous body fluids through the microchannel. For this reason, such microfluidic elements may be provided with a hydrophilic surface coating. The surface coating should in addition be biocompatible and sterilizable and should allow the microchannel to be filled within a very short period.

Finally, an adequate long-term stability of the surface coating is desirable. Hydrophilic coatings usually have high-energy surfaces. This is thermodynamically unfavorable because the surface tries to reduce its high energy by reducing the hydrophilicity. This occurs, for example, by the adsorption of apolar gas molecules. Packaging materials and in particular polymeric packaging materials can, however, contain a considerable proportion of apolar gases which escape over time from the packaging material. In addition, air is always enclosed in the packaging. It is therefore desirable to reduce the proportion of undesired gases in the packaging.

Desiccants such as activated carbon, silica gels and molecular sieves are generally used to adsorb undesired gases in packaging (cf. EP 0 951 939 A2). However, the use of these materials can be problematic for objects with a hydrophilic surface coating for medical purposes such as microneedles or lancets. In addition, it is unclear to what extent the particularly undesired apolar gases are reduced.

Hence, the present disclosure describes a package for an object having a hydrophilic surface. The package maintains the hydrophilicity of the surface during a storage period and is simple to produce and to use. In particular, the package facilitates the use of disposable microfluidic test elements in analytical systems.

In one embodiment, the package includes at least one loose cover and/or at least one adsorbing surface, the affinity of which for apolar gases is equal to or greater than that of the hydrophilic surface of the object.

It has surprisingly turned out that even a loose cover (i.e., one which is not glued or otherwise attached such as a cover plate or cover fleece) is sufficient as a screen to impede the apolar gases from gaining access to the hydrophilic surface of the packaged object to such an extent that the hydrophilicity of the surface remains reliably stable even over long periods. One only has to take care that the loose cover does not itself release any apolar gases.

The same result is achieved when an additional adsorbing surface is present within the package which itself adsorbs apolar gases at least equally as well as the hydrophilic surface of the packaged object.

The package according to the present disclosure can reduce the adsorption of apolar gases onto the hydrophilic surface in a particularly simple and effective manner such that the package is well-suited for medical mass products without excessively increasing the costs.

According to another embodiment of the present disclosure, the at least one adsorbing surface is designed in the form of at least one adsorber element having an adsorbing surface that is packaged with the object. Such an adsorber element, for example in the form of a small plate or fleece, can be automatically added in a simple manner when the object having a hydrophilic surface is packaged.

The at least one adsorber element can, in particular, be in the form of a cover for the hydrophilic surface itself such that the access of apolar gases to the hydrophilic surface is additionally impeded.

In another embodiment, the at least one adsorber element can have an adsorber layer in the form of a hydrophilic coating. In this case the hydrophilicity (i.e., the surface energy) of the adsorber layer should be equal to or greater than the hydrophilicity (i.e., the surface energy) of the surface of the packaged object in order to ensure an effective adsorption of the apolar gases to the adsorber layer. The hydrophilic coating can consist of the same material as the hydrophilic surface of the packaged object so that the adsorber layer is automatically biocompatible and sterilizable.

Another embodiment of the adsorber layer according to the disclosure is a hydrophilic coating on at least a portion of the inside of the package with a hydrophilicity or surface energy equal to or greater than the hydrophilicity or surface energy of the surface of the packaged object to ensure an effective adsorption of the apolar gases to the adsorber layer. Also in this case the hydrophilic coating can consist of the same material as the hydrophilic surface coating of the packaged object so that the adsorber layer is automatically biocompatible and sterilizable.

Numerous materials are generally known for hydrophilic coatings such as, for example, lecithin or dextran sulfate. Particularly suitable materials which can be present in a hydrophilic coating or of which a hydrophilic coating can consist, are polyacrylic acids and polyacrylates. These are biocompatible and sterilizable and therefore particularly well-suited, especially for coating packaging in the medical field or for microfluidic systems having hydrophilic surface coatings such as, for example, microneedles for portable blood sugar measuring instruments.

The present disclosure also concerns the unit including a package with contents (i.e., a package containing a microfluidic element having a hydrophilic surface for taking up a body fluid and at least one loose cover which covers the hydrophilic surface and/or at least one adsorbing surface, the affinity of which for apolar gases is equal to or greater than that of the hydrophilic surface).

The teachings of the present disclosure will be better understood upon reference to the following description on the basis of the embodiment example shown schematically in the drawings.

DETAILED DESCRIPTION OF EMBODIMENTS OF THE DISCLOSURE

Figure 1:
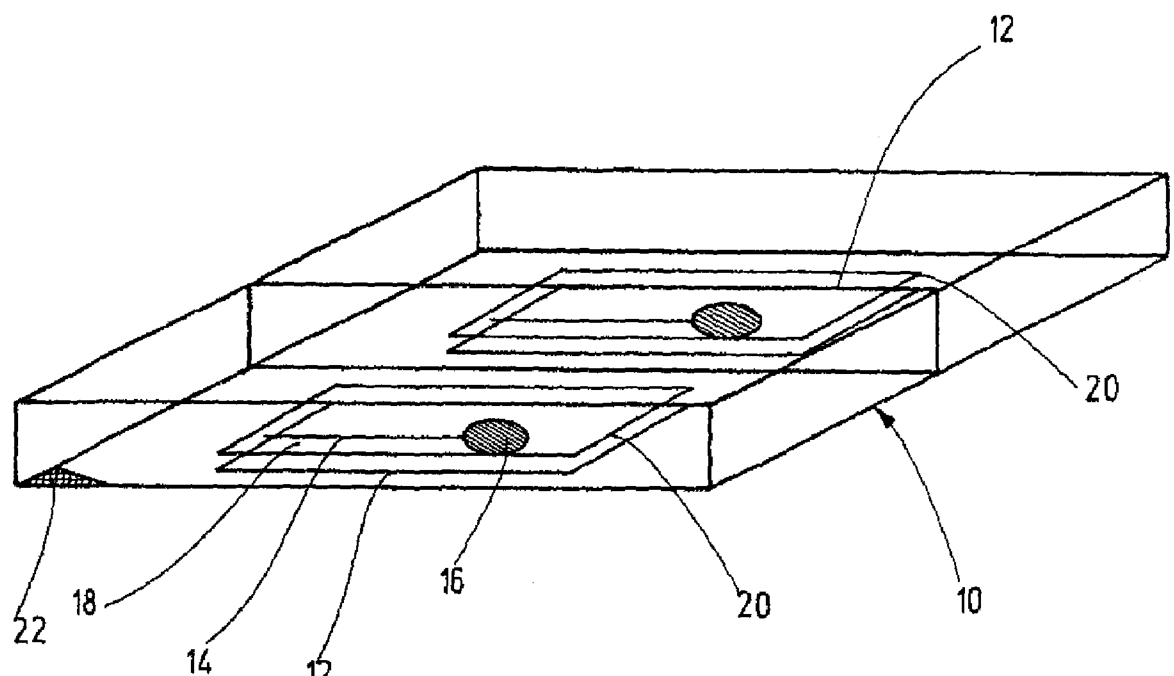
FIG. 1 shows a package for microfluidic elements in a diagrammatic view.

The package 10 shown in FIG. 1 can, for example, be designed in the form of a blister magazine for separately holding a plurality of microsamplers 12. A blister magazine is known from WO 2005/104948. It could also be conceivably used in the form of a drum magazine according to EP 0951939. Reference is explicitly made to the said documents in this connection.

The microsampler 12 is provided for collecting a small amount of blood from a body part. It can consist of a thin stainless steel sheet in which a longitudinally open groove-shaped capillary channel 14 leads from a distal tip to a proximal collecting site 16 which can be designed as a reaction area for the detection of an analyte (e.g., glucose). Optionally, the collected blood can also be transferred into an analytical unit (not shown) in order to determine the analyte there. A hydrophilic surface 18 enables an improved liquid transport at least in the area of channel 14 and collecting site 16. For this purpose, the hydrophilicity of surface 18 should be maintained over the intended storage period such that a contact angle of less than 40° is achieved with deionized water.

In general, hydrophilic surfaces are always also high energy surfaces. Since natural systems try to minimize their energy, hydrophilic surfaces become hydrophobized by adsorption of apolar gases or by contamination with dust or other fine particles. Hence, according to the disclosure, hydrophilic surface 18 is kept hydrophilic over time by storage in the envelope of a suitable package 10. For this purpose, a loose cover 20 in the form of a small cover plate is placed over the side of microsampler 12 provided with hydrophilic surface 18 in package 10. Cover 20 can form a mechanical barrier or it can act as an adsorber element with a hydrophilic coating, the hydrophilicity of which is equal to or greater than the hydrophilicity of surface 18.

It is also possible that the adsorbing surface is provided in the form of a hydrophilic coating 22 on at least a part of the inside of package 10, the hydrophilicity of which is equal to or greater than the hydrophilicity of surface 18. For the sake of simplicity, only a section of coating 22 is shown in FIG. 1. Hydrophilic coating 22 may consist of at least one linear or cross-linked polyacrylic acid and/or at least one linear or cross-linked polyacrylate.

Figure 2:
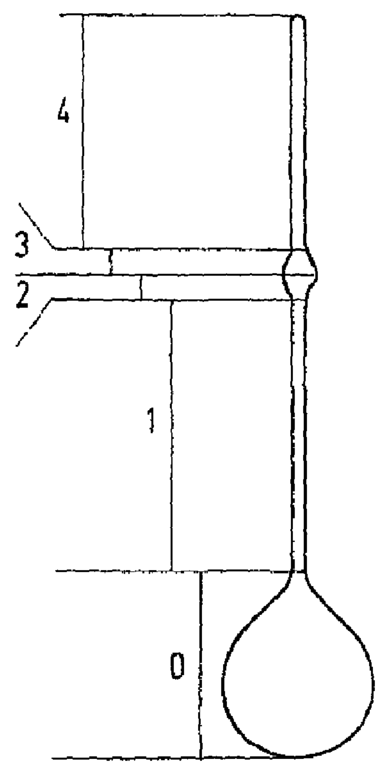
FIG. 2 shows a schematic representation of a small test plate with defined capillary regions.

For a comparison experiment, small test plates made of medical steel were provided with a reservoir and a groove-shaped capillary. These structures were divided into five regions as shown in FIG. 2. Region 0 comprises the reservoir. Region 1 comprises the lower part of the capillary. Regions 2 and 3 comprise a widening of the capillary. Region 4 comprises the upper part of the capillary. One half of the small test plates were coated with lecithin using a method known to a person skilled in the art and the other half of the small test plates were coated with dextran sulfate. Subsequently, the test slides were packaged in Mylar foil (manufacturer: DuPont) with a thickness of 20 μm. In each case, one half of the small plates coated with lecithin and dextran sulfate were packaged unprotected and the other half were provided with a cover plate according to the present disclosure to protect the capillary. Hence, four different types of packaged small test plates were present:

a) coated with lecithin without protection;

b) coated with lecithin with cover plates;

c) coated with dextran sulfate without protection; and d) coated with dextran sulfate with cover plates.

The finally packaged small test plates were sterilized with electron beams (β-rays) (25 kGy, 10 meV) and stored for 12 weeks at 35° C. This simulated a storage for two years at room temperature.

Each second week the small plates were removed and tested. For this 1.5 μl of blood was pipetted into the reservoir of the capillaries and the filling behaviour of the capillaries was evaluated on the basis of the division into regions 0 to 4 shown in FIG. 2 and described above.

Figure 3:
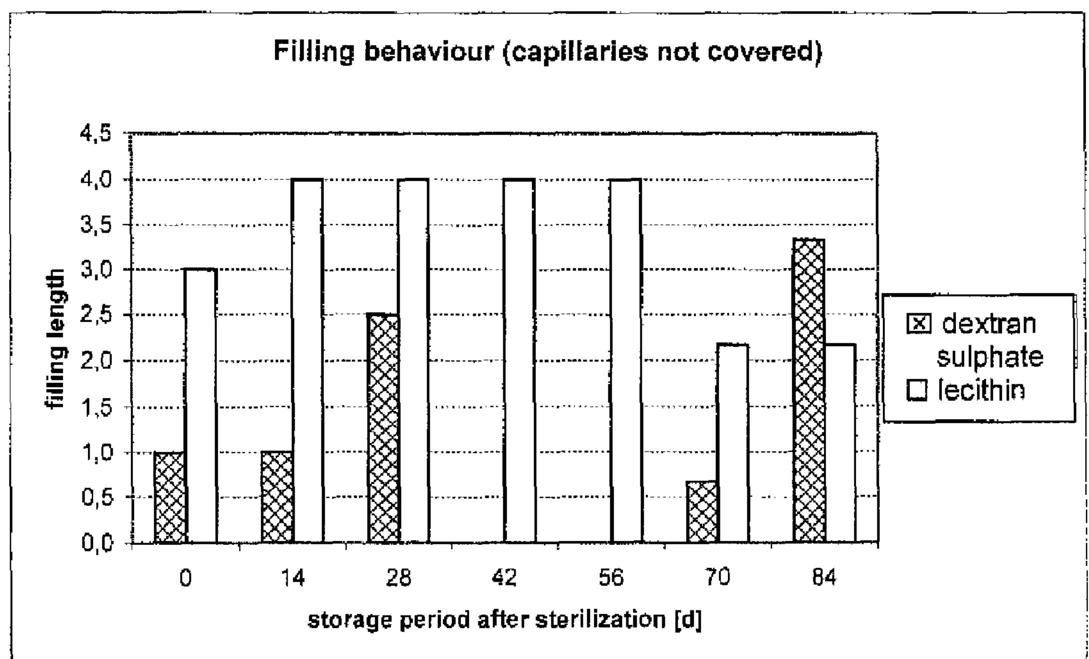
FIG. 3 shows a column diagram of the filling behavior of a microfluidic element without a protection for the hydrophilic surface.
Figure 4:
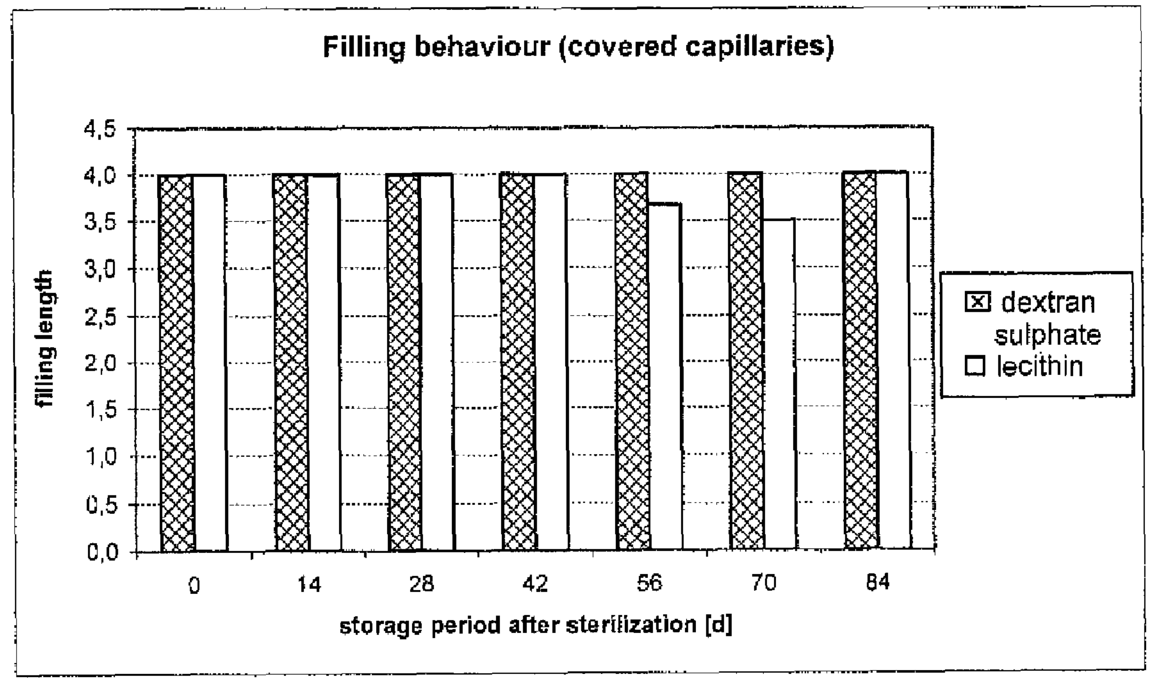
FIG. 4 shows a column diagram of the filling behavior of a microfluidic element with a protection for the hydrophilic surface.

The results are shown as column diagrams in FIGS. 3 and 4. It can be readily seen that the protected capillaries still completely fill even after the maximum storage period when they are provided with the dextran sulfate coating and completely or almost completely fill when they are provided with the lecithin coating. In the case of the unprotected capillaries, those with the lecithin coating performed better, but the filling behaviour was overall considerably worse than that of the dextran coated capillaries (i.e., the capillaries only partially fill or do not fill at all).

The invention claimed is:

1. A package including:

an interior region including an object having a microfluidic element for taking up a body fluid, the element having a hydrophilic surface with a first affinity for apolar gases; and at least one of a loose cover for the hydrophilic surface and an adsorbing surface within the package, the affinity of which for apolar gases is equal to or greater than the first affinity for apolar gases.

2. The package according to claim 1, wherein the loose cover is in the form of one of a cover plate and a cover fleece.

3. The package according to claim 1, wherein the adsorbing surface is in the form of an adsorber element having an adsorbing surface that is packaged with the object.

4. The package according to claim 3, wherein the adsorber element forms a loose cover for the hydrophilic surface.

5. The package according to claim 3, wherein the adsorber element is provided with a hydrophilic coating having a hydrophilicity that is at least as great as a hydrophilicity of the hydrophilic surface.

6. The package according to claim 1, wherein the adsorbing surface includes a hydrophilic coating of at least a portion of the interior of the package, the hydrophilic coating having a hydrophilicity that is at least as great as a hydrophilicity of the hydrophilic surface.

7. The package according to claim 5, wherein the hydrophilic coating contains at least one of a linear and a cross-linked polyacrylic acid and at least one of a linear and a cross-linked polyacrylate.

8. The package according to claim 5, wherein the hydrophilic coating contains at least one of a polyacrylic acid and a polyacrylate.

9. The package according to claim 5, wherein the hydrophilic coating includes at least one of a linear polyacrylic acid, a cross-linked polyacrylic acid, a linear polyacrylate, and a cross-linked polyacrylate.

10. The package according to claim 5, wherein the hydrophilic coating consists of the same material as the hydrophilic surface of the object.

11. The package according to claim 1 wherein the hydrophilic surface forms a contact angle of less than 80° with deionized water.

12. The package according to claim 1, wherein the hydrophilic surface forms a contact angle of less than 40° with deionized water.

13. The package according to claim 1, wherein the package includes a magazine for a plurality of microfluidic elements.

14. A method of performing a blood sugar measurement, including the steps of:

obtaining a microfluidic element having a hydrophilic surface from a package having at least one of a loose cover for the hydrophilic surface and an adsorbing surface within the package, the affinity of which for apolar gases is equal to or greater than an affinity for apolar gases of the hydrophilic surface;

obtaining a blood sample using the microfluidic element; and measuring blood sugar based on the behavior of a reaction area on the microfluidic element.

15. A package for maintaining, during a storage period, the hydrophilicity of a hydrophilic surface of a microsampler used to collect a bodily fluid, the package including:

at least one interior region having a microsampler for collecting a bodily fluid, the microsampler having a hydrophilic surface with a first affinity for apolar gases; and an element configured to maintain the hydrophilicity of the hydrophilic surface of the microsampler, the element being at least one of a cover located relative to the surface to form a mechanical barrier for the surface and an adsorbing surface within the at least one interior region;

wherein the element has an affinity for apolar gases that is at least as great as the first affinity for apolar gases.

16. The package according to claim 15, wherein the cover is one of a cover plate or cover fleece.

17. The package according to claim 15, wherein the adsorbing surface is formed on an adsorber element located within the interior region.

18. The package according to claim 17, wherein the adsorber element forms a loose cover for the hydrophilic surface.

19. The package according to claim 15, wherein the adsorbing surface includes a hydrophilic coating having a hydrophilicity that is at least as great as the hydrophilicity of the hydrophilic surface.

20. The package according to claim 15, wherein the adsorbing surface includes a hydrophilic coating of at least a part of the interior region, the hydrophilic coating having a hydrophilicity that is at least as great as the hydrophilicity of the hydrophilic surface of the microsampler.

21. The package according to claim 19, wherein the hydrophilic coating contains at least one of a linear polyacrylic acid, a cross-linked polyacrylic acid, a linear polyacrylate and a cross-linked polyacrylate.

22. The package according to claim 19, wherein the hydrophilic coating includes at least one of a linear polyacrylic acid, a cross-linked polyacrylic acid, a linear polyacrylate and a cross-linked polyacrylate.

23. The packaging according to claim 19, wherein the hydrophilic coating consists of the same material as the hydrophilic surface of the microsampler.

24. The package according to claim 15, wherein the hydrophilic surface is maintained in such a manner that it forms a contact angle of less than 80° with deionized water.

25. The package according to claim 24, wherein the contact angle is less than 40° with deionized water.

26. The package according to claim 15, wherein the package includes a plurality of interior regions, thereby forming a magazine for maintaining a corresponding plurality of microsamplers.

* * * * *